(12) United States Patent
Long

(10) Patent No.: US 6,440,901 B1
(45) Date of Patent: Aug. 27, 2002

(54) CALCIUM CHLORIDE FRUIT BLOSSOM THINNING AGENT

(76) Inventor: Gary S. Long, 4302 Scenic Dr., Yakima, WA (US) 98908

( * ) Notice: Subject to any disclaimer, the term of this patent is extended or adjusted under 35 U.S.C. 154(b) by 0 days.

(21) Appl. No.: 09/650,474

(22) Filed: Aug. 29, 2000

(51) Int. Cl.$^7$ .......................... A01N 3/02; A01N 59/08; A16K 33/14
(52) U.S. Cl. ...................................... 504/116; 424/663
(58) Field of Search .......................... 504/116; 424/663

(56) References Cited

U.S. PATENT DOCUMENTS

| | | | |
|---|---|---|---|
| 4,819,373 A | 4/1989 | Kadkade | 47/58 |
| 5,118,340 A | 6/1992 | Butselaar et al. | 71/121 |
| 5,242,891 A | 9/1993 | Larsen | 504/127 |

FOREIGN PATENT DOCUMENTS

WO  9932419  * 7/1999

OTHER PUBLICATIONS

"NC 99" product label, Genesis Agri–Products Inc., Union Gap, WA.

Jim McFerson and Troy Schmidt, "Organic and Non–Organic Chemical Bloom Thinners In apple," Washington State Horitculture Association Poster Session Abstracts 1999, p. 20.

"2000 Crop Protection Guide for Tree Fruits in Washington" Washington State University Cooperative Extension, College of Argiculture & Home Economics.

"Apple Fruit Thinning," http://www.hort.vt.edu/graduate/daward2/fruitfiles/thinning.html.

Dr. Kathleen Williams, "Growth Regulator Sprays; Blooms Thinning Programs for Apples" http://www.tfrec.wsu.edu/Horticulture/bloomthin.html.

"Apple Fruit Thinning," http://www.ento.vt.edu/Fruitfiles/THINNING.html.

Dr. Kathleen Williams, "Apple Postbloom Thinning," http://www.tfrec.wsu.edu/Horticulture/postbloom.html.

Stephen M. Southwick et al., "chemical Thinning of 'Loadel' Cling Peach [Prunus Persica (I.) Batsch] With Armothin®," http://fruitsandnuts.ucdavis.edu/south1.html.

* cited by examiner

Primary Examiner—Alton Pryor
(74) Attorney, Agent, or Firm—Stratton Ballew PLLC

(57) ABSTRACT

A process and composition for thinning fruit blossoms with a calcium chloride solution is provided. The calcium chloride is a common salt, often referred to as CaCl, but having the chemical formula $CaCl_2$ and is preferably applied to the blooms in a solution or brine. The calcium chloride brine is a natural material that is classified as a "generally regarded as safe" (GRAS) compound. The calcium chloride solution in water apparently interrupts the pollination of blooms through the dessication of the pistils, when it is applied during the blooming period. The $CaCl_2$ blossom or bloom thinning agent solution is effective on many varieties of fruit trees, especially apples. The calcium chloride is preferably applied in a substantially aqueous solution at a rate of between 5 and 40 pounds of calcium chloride per acre. The $CaCl_2$ solution is not an artificial or derived substance and carries none of the environmental and health concerns raised by other hormonal or caustic chemical thinning agents.

15 Claims, 4 Drawing Sheets

CALCIUM CHLORIDE FRUIT BLOSSOM THINNING AGENT

TECHNICAL FIELD

The invention relates to a process and composition for the thinning of fruit blooms, and more particularly to the use of a calcium chloride solution for the natural thinning of fruit blossoms.

BACKGROUND OF THE INVENTION

Under most conditions, fruit and nut trees will produce an over-abundant crop. This over production results in small, low quality fruit, often poorly colored. The thinning of fruit blossoms prevents this over-production and promotes annual bearing, instead of fruit production that fluctuates year to year. Thinning also increases fruit size and color. For fruit trees, bloom thinning also increases tree vigor, and reduces limb breakage and winter injury. Because of these benefits, chemical bloom thinning practices are quite common, but are expensive and must be applied with care.

Most conventional chemical products employed for the thinning of blossoms on plants such as fruit trees can produce unwanted effects beyond thinning. Chemical thinning uses either caustic materials or hormonal type growth regulators to reduce the quantity of fruit in a particular crop. Most hormonal type thinners are quickly losing acceptance, with many hormonal thinners currently banned or under the scrutiny of several groups concerned about effects on the products to which they are applied. Caustic thinners either employ weakly acidic compounds or desiccating formulations to chemically dry or "burn" the blossoms. Bloom desiccation apparently prevents pollination and inhibits seed formation.

Generally, thinning is a naturally occurring phenomenon for most food crops. The variety and strain of the plant or tree, health and proximity to pollenizers all dictate the fruit "set" or quantity of blooms that can develop into a mature fruit. Additionally, climatic factors, such as wind, precipitation, and primarily temperature can all act as natural thinners to reduce the number of blooms available for pollination and eventual maturation into a salable product. However, natural thinning is unreliable and inconsistent, especially in moderate climates.

Consistent and controlled thinning is especially critical in fruit tree crops, where each fruit competes for resources from the tree. Too high of a fruit set on individual trees drastically reduces the size of each fruit and so reduces the sizing grade of the crop. Failure to make a sizing grade can eliminate any chance of profit for an orchardist.

For fruit trees, only a limited number of caustic chemical bloom thinners are currently available or in the registration process. The pursuit of registration through the United States Environmental Protection Agency (USEPA) can be a long and expensive process. The typical orchardist has few options in thinning. Fewer still are the thinning options available to organic orchardists, which cannot utilize any compound that fails to acquire an "all natural" designation.

For fruit trees, manual thinning can be performed to reduce or eliminate the need for chemical thinners. However, the expense of manual thinning is considerable and the availability of skilled workers that can efficiently thin tree fruits decreases every year. Effective and affordable chemical bloom thinning alternatives are needed for both the conventional and organic orchardist.

In Washington state, for example, fruit tree crops such as apples may soon be allowed to employ ammonium thiosulfate (ATS) for bloom thinning. ATS is considered a generally effective and consistent caustic chemical type of bloom thinner. However, ATS is not classified a natural or "organic" compound and so cannot be used by organic orchards.

A combination of fish oil and lime sulfur is an alternative to ATS that currently meets the criteria for use as an organic compound. A significant problem encountered with fish oil and lime sulfur is that the results of any particular application can vary considerably. Applications of fish oil and lime sulfur are not repeatable to produce the same effect under what appear to be identical conditions. According to field trials by the Washington Tree Fruit Research Commission, damage from fish oil and lime sulfur can result in a wide range of effects that can include significant over-thinning and injury to the developing fruit and leaves, such as russeting and wilting. Alarmingly, the same treatment of the caustic oil/sulfur mix, which injured fruit under similar conditions, may at another time produce no measurable fruit thinning effects at all. A chemical fruit thinner, which relies on caustic rather than hormonal mechanisms to thin fruit, is needed that provides consistent and predictable thinning results.

Naphthaleneacetic acid (NAA) is a widely utilized chemical bloom thinner that employs the hormonal and acidic properties of the compound to thin the blossoms. NAA was first used to delay preharvest drop and then later found to be an effective bloom thinner. Similar to NAA is napthaleneacetamide (NAD or NAAm). Both NAA and NAD are often combined with the insecticide Carbaryl to increase the efficacy of the thinners. This combination is especially worrisome, in that Carbaryl, which is sold under the trade name Sevin®, is toxic to bees, predatory mites and most importantly, farm workers Prior U.S. patents that cite fruit thinning properties for caustic type fruit thinning agents include U.S. Pat. No. 3,958,007 to Wommack, which teaches the pesticidal use of a particular family of substituted alkyl, 4-3-thioallophanates. Additionally, Wommack suggests that a salt of these substituted compounds can be applied in a mixture with thinning compounds. U.S. Pat. No. 5,118,340 to Butselaar '340 discloses that the chloride salts of alkoxylated amines can thin the blossoms of certain stone fruits. These prior patents employ salts of the active ingredients to better achieve solution into water for application. These previously disclosed active ingredients may be effective compounds for thinning fruits, especially tree fruits. Like the currently utilized chemical bloom thinners, these patents suggest compounds that are expensive to synthesize or separate. Importantly, none of these prior bloom thinning compounds include a guarantee of environmental safety nor are they intrinsically free of unwanted effects, beyond their intended purpose.

SUMMARY OF INVENTION

The present invention provides a process and composition for thinning fruit blossoms with a calcium chloride solution. The calcium chloride salt is actually a di-chloride, having a chemical formula of $CaCl_2$. Calcium chloride is preferably applied to the blooms in a solution or brine. The calcium chloride brine, applied by the present invention, is a natural material that is classified as a "generally regarded as safe" (GRAS) compound. The calcium chloride solution in water has the apparent ability to interrupt the pollination of blooms through the dessication of the pistils, when it is applied during the blooming period. The $CaCl_2$ blossom or bloom thinning agent solution is effective on many varieties of fruit bearing plants, especially fruit bearing trees, such as apple trees.

The present invention thins fruit blossoms by applying an effective amount of the blossom thinning composition to the blossoms of a fruit bearing plant. The blossom thinning composition includes calcium chloride ($CaCl_2$) as an active ingredient for the purpose of blossom thinning. The calcium chloride is preferably applied in a substantially aqueous solution, at a rate of between 5 and 40 pounds of calcium chloride per acre of the fruit bearing plant. A preferred, final mixture of the calcium chloride includes approximately 1 pound of $CaCl_2$ per 10 gallons of water.

The $CaCl_2$ solution applied to blossoms by the present invention has a great advantage over other, conventional thinning agents in that it is not an artificial or derived substance and carries none of the environmental and health concerns raised by other hormonal or caustic chemical thinning agents.

DETAILED DESCRIPTION OF SPECIFIC EMBODIMENTS

Figure 1:
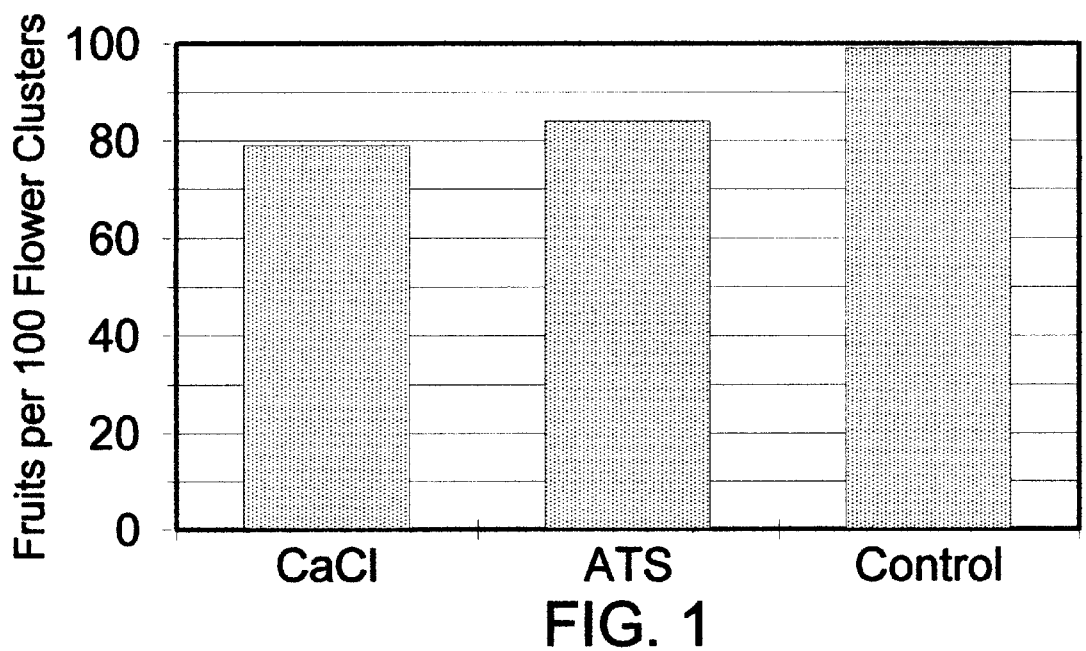
FIG. 1 is a graph titled "Fruit Set Fuji Apple Bloom Thinners," which shows some of the results of a field trial, as described in Example 1.

The invention provides a process and a composition for thinning fruit blossoms. The process of the invention includes applying an effective amount of a blossom thinning composition to the blossoms of a fruit bearing plant, the blossom thinning composition including calcium chloride. Calcium chloride is a common salt that is often referred to as CaCl. However, calcium chloride is actually a di-chloride, having a chemical formula of $CaCl_2$. Preferably, the calcium chloride is applied to the blooms in a water diluted formulation that begins with a concentrated aqueous solution or "brine."

The calcium chloride brine has the apparent ability to interrupt the pollination of blooms through the dessication of the pistils, when it is applied during the blooming period or stage. This mechanism is widely preferred over the hormonal compounds or compounds that mimic the action of hormones in bloom thinning. A potential disadvantage of dessication is the potential of "burn" or drying damage to the remaining fruit and leaves. The thinning compound of the present invention has the advantage of exhibiting little or no damage to the leaves or remaining fruit, when it is applied with accepted practices and according to labeling instructions.

An additional advantage of the calcium chloride compound of the present invention is that it supplies the fruit with needed nutrients, directly to the developing fruit. Calcium is an essential mineral in the development of most fruits. For apples, the crispiness required by the discriminating consumer is a direct result of the calcium content of the apple. Also for apples, the characteristic bright red color is also dependent upon the availability of calcium throughout the growth of the apple. The calcium chloride thinning agent solution expected to be effective on many varieties of fruit bearing plants and is proven to be especially effective on fruit bearing trees, such as apples. The calcium chloride solution has a great advantage over other, conventional thinning agents in that it is not an artificial or derived substance and carries none of the concerns raised by other hormonal and chemical thinning agents.

Calcium chloride brine is a natural material, classified as a "generally regarded as safe" (GRAS) compound. The Food Drug and Cosmetic Act (21 CFR), as enforced by the United States Food and Drug Agency (FDA) cites $CaCl_2$ as a "multipurpose GRAS food substance (21 CFR 184.1193) and a "general purpose food additive" (21 CFR 582.1193), when used in accordance with good manufacturing practice (21 CFR 184.1 (b)(1)). Calcium chloride is considered benign to bee and predatory mite populations, as well as safe for orchard workers, requiring no delayed re-entry period after application. Precautions are suggested for working with calcium chloride due to its mild caustic properties. These precautions include goggles and respirator to prevent irritation of the eyes or respiratory tract.

Alternatively, calcium chloride is commercially available in a variety of forms. Anhydrous pellets of substantially pure, (greater than 90%, by weight) calcium chloride are available in bulk quantities. A hydrated calcium chloride product ($CaCl_2 \cdot 2H_2O$) is also available in commercial volumes, which is a flake form that contains approximately 77% calcium chloride, by weight.

For tree fruit bloom applications, the calcium chloride is applied in a formulation that is preferably a substantially aqueous solution. The calcium chloride bloom thinning solution can be mixed on site in the spray tank, or delivered and stored in aqueous solution, to insure proper mixing and consistent dilution, as preferred. Most preferably, this bloom thinning solution is stored in a concentrate brine containing approximately 35% $CaCl_2$, by weight. Higher brine concentrations can be utilized. However at too high of brine concentration, salt precipitation can occur, which can lead to mixing problems.

A preferred composition of the concentrated brine corresponds to a 13% weight to weight ratio of solvated calcium to the total solution. The bloom thinning solution preferably contains the calcium chloride brine, at a concentration of between 2 to 8 gallons of the 13% brine per 200 gallons of water per acre of tree fruit. A preferred application rate, as used in the following field trial examples, is 5 gallons of the 13% calcium chloride brine per 200 gallons of water per acre, which corresponds to an approximate concentration of 2.5% calcium chloride brine to total solution, in a volume to volume relation. With the 13% brine concentrate at approximately 11.2 pounds per gallon, the final, applied concentration corresponds to approximately 1 pound of $CaCl_2$ per 10 gallons of water, or alternatively, approximately 20 pounds of $CaCl_2$ per acre.

These preferred rates can vary greatly, given the maturity of the trees, the cultivar variety and the desired efficacy or amount of thinning needed. Application rates as low as, or lower than a quarter pound of $CaCl_2$ per 10 gallons of water, or alternatively 5 pounds of $CaCl_2$ per acre, are certainly within the scope of the invention. Also, application rates and as high as, or higher than 2 pounds of $CaCl_2$ per 10 gallons of water, or alternatively 40 pounds of $CaCl_2$ per acre, are certainly within the scope of the invention.

A slightly stronger solution of 6 gallons of the calcium chloride brine to 200 gallons of water per mature acre of tree fruit is most preferred. This solution is applied at bloom with a conventional "tank sprayer." A second application can also be applied after five days.

Adjuvants can also be added to the calcium chloride bloom thinning solution. The adjuvants can facilitate spreading and efficacy, and improve the adhesion or sticking properties of the composition. "Spreader-stickers" is a term often used to describe this category of adjuvants that for the purposes of this application can also include oils, antifoaming agents and surfactants.

A series of field trials comparing the calcium chloride composition of the present invention to other alternative chemical thinners were performed to verify efficacy as a bloom thinner. The trials followed labeling recommendations and best management practices for all applications. Two of these trials are discussed as follows, but are not intended to specifically limit the invention:

EXAMPLE 1

A first field trial to test the effects of calcium chloride as a bloom thinning agent was performed in an orchard located in East Wenatchee, Washington, by the Washington Tree Fruit Research Commission on a commercial block of a Fuji apple cultivar of the variety "WVC." Two areas of the block's apples were each treated with two alternative chemical thinning compounds. Calcium chloride was used in the first area. Ammonium thio-sulfate (ATS) was used in the second area. A third area of the apple block was utilized as a control group and treated with water. The treatments were all performed with conventional test methodologies and procedures.

Figure 3:
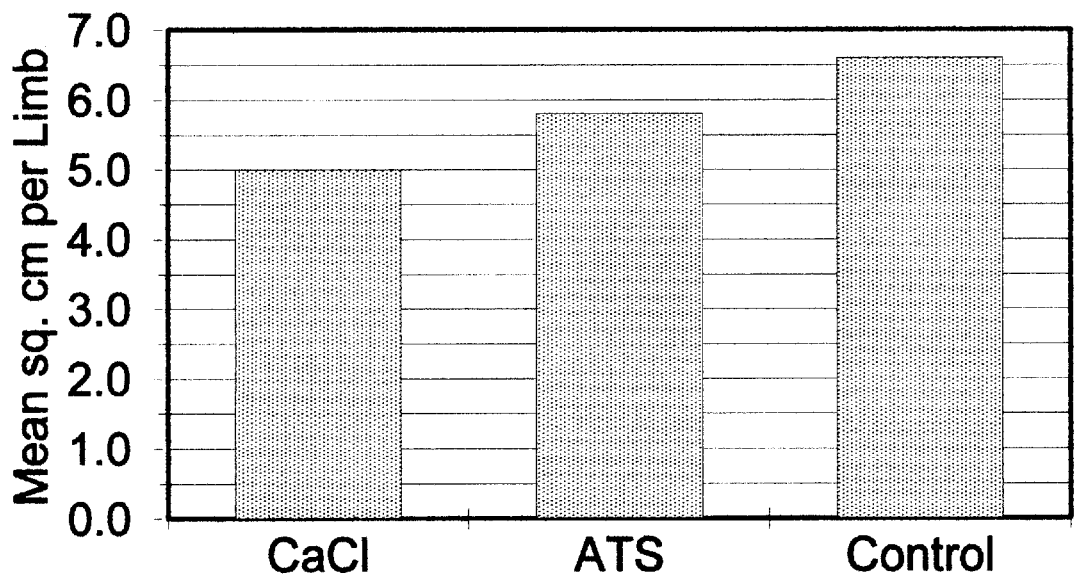
FIG. 3 is a graph titled "Total Fruit Surface Area Fuji Apple Bloom Thinners," which shows some of the results of a field trial, as described in Example 1.

Other than the application of the thinning compounds, all three blocks were managed without differentiation. All treatments were applied utilizing standard airblast sprayers and spreader-stickers as appropriate. The experiments were in a randomized complete block design with 2 to 4 replications. Both ATS and calcium chloride treatments showed similar types of desiccation damage on blossom, fruitlet, and leaf tissue. Results of this trial are listed in TABLE 1 and shown in the graphs of FIGS. 1 and 3. The results of the trial are reported in an industry standard format, employing conventional sampling and reporting criteria and also using standard statistical methods.

EXAMPLE 2

Figure 2:
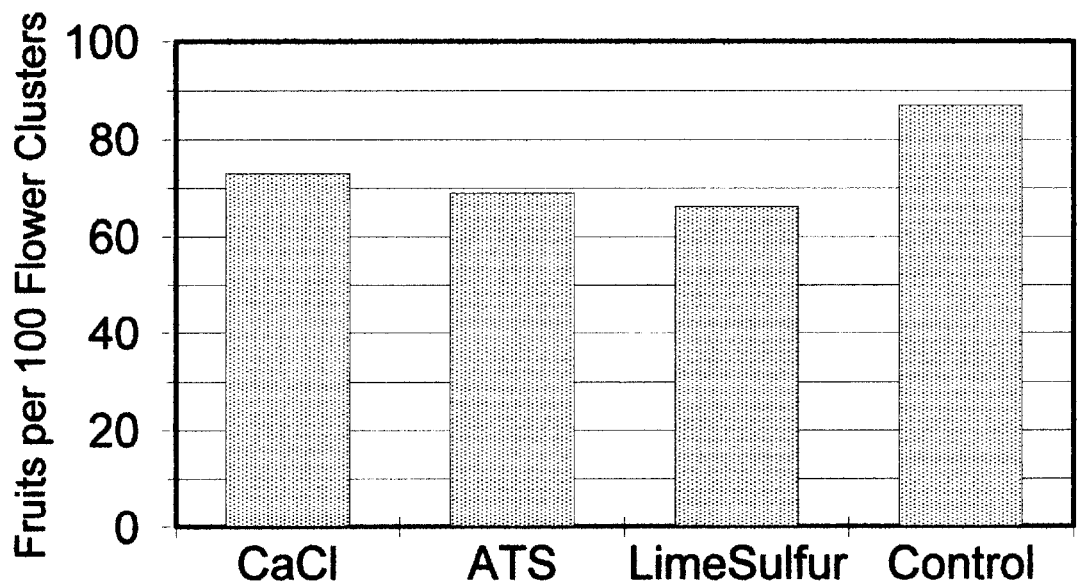
FIG. 2 is a graph titled "Fruit Set Red Delicious Apple Bloom Thinners," which shows some of the results of a field trial, as described in Example 2.
Figure 4:
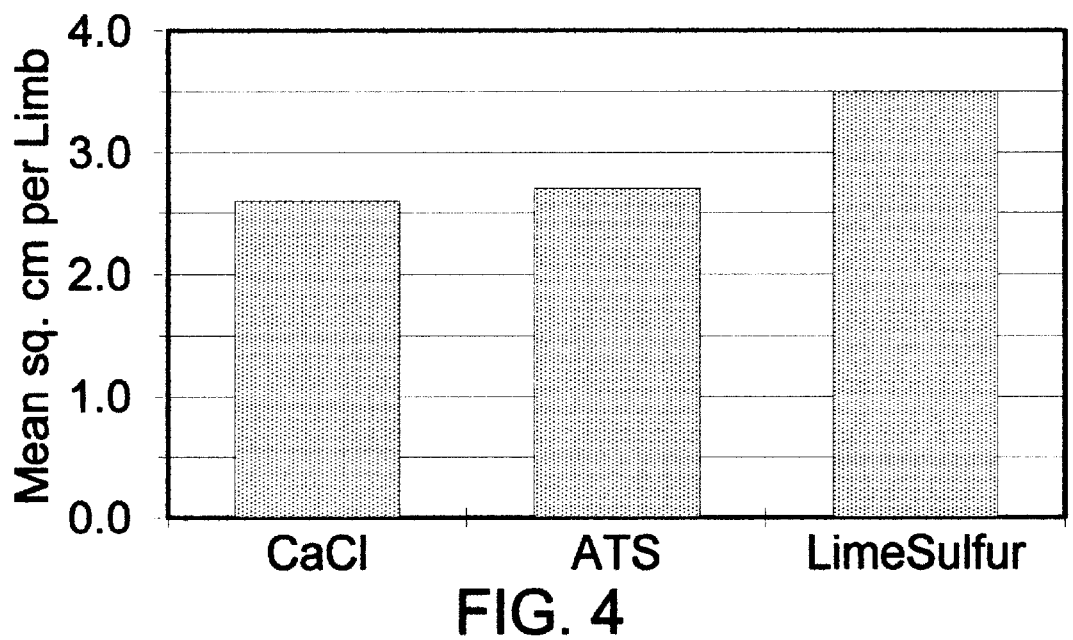
FIG. 4 is a graph titled "Total Fruit Surface Area Red Delicious Apple Bloom Thinners," which shows some of the results of a field trial, as described in Example 2.

A second field trial to test the effects of calcium chloride as a bloom thinning agent was performed at an orchard located in Azwell, Washington, by the Washington Tree Fruit Research Commission on a commercial block of a Red Delicious apple cultivar of the variety "Lutz." Three areas of the block's apples were each treated with one of three alternative chemical thinning compounds. Ammonium thio-sulfate was used in the first area. Calcium chloride was used in the second area and "Crocker's" lime and sulfur was used in the third area. A fourth area of the apple block was utilized as a control group and treated with water as a control. The treatments were all performed with conventional test methodologies and procedures. Other than the application of the thinning compounds, all four blocks were managed without differentiation. Results of this second trial are listed in TABLE 2 and shown in the graphs of FIGS. 2 and 4. The results of the trial are reported in an industry standard format, employing conventional statistical methods.

TABLE 2

Result Summary of Chemical Thinning Trials for "Lutz" Red Delicious Apples

| Treatment | Mean Fruit Area per Limb (cm$^2$) | Mean Fruit per 100 Clusters | % Flower Clusters Blanked | % Flower Clusters Singled | % Flower Clusters Doubled | % Flower Clusters Tripled | % Flower Clusters w/4+ Fruit |
|---|---|---|---|---|---|---|---|
| CaCl | 2.6 | 73 | 41.7 | 44.4 | 12.7 | 1.0 | 0.2 |
| ATS | 2.7 | 69 | 47.0 | 38.8 | 12.8 | 1.5 | 0.0 |
| Control | 3.5 | 87 | 35.7 | 44.9 | 17.2 | 1.9 | 0.4 |

For both of the above trials, it was observed that damage from the "Crockers" fish oil and lime sulfur treatments were more varied by comparison to ATS. The researchers observe that significant over-thinning and russeting results from the oil and sulfur treatments. From these experimental results, along with additional feedback regarding time required per tree for hand thinning, the researchers concluded that there were no consistent, significant differences between ATS and calcium chloride bloom thinning treatments. However, significant differences were observed in the water control, which in some cases also exhibited a significant increase in the number of single fruitlets per cluster.

Additionally overall, no consistent significant differences due to treatments were found for fruit length, weight, as expressed in a length over diameter (L/D) ratio, or harvest quality parameters. The fruit for each thinner tested, including the calcium chloride, minimally impacted the reported average L/D ratio.

These field trial results also indicate that calcium chloride could provide bloom thinning equivalent to ATS and provide apple growers with effective and organically-acceptable bloom thinners. The field trials show that calcium chloride

TABLE 1

Result Summary of Chemical Thinning Trials for "WVC" Fuji Apples

| Treatment | Mean Fruit Area per Limb (cm$^2$) | Mean Fruit per 100 Clusters | % Flower Clusters Blanked | % Flower Clusters Singled | % Flower Clusters Doubled | % Flower Clusters Tripled | % Flower Clusters w/4+ Fruit |
|---|---|---|---|---|---|---|---|
| CaCl | 5.0 | 79 | 40.0 | 45.5 | 12.5 | 2.0 | 0.1 |
| ATS | 5.8 | 84 | 38.2 | 47.4 | 11.9 | 1.9 | 0.7 |
| Control | 6.6 | 99 | 28.1 | 53.2 | 12.7 | 4.2 | 1.8 | can also be combined with applications of fish oil/lime sulfur combinations to provide apple growers with an effective and organically acceptable bloom thinner.

Other crops besides apples will benefit form the calcium chloride bloom thinner of the present invention. Because any bloom will assuredly desicate and be thinned from the application of the brine solution of the present invention, the applications for effective bloom thinning will most likely include any tree fruit, and very likely to include any fruit bearing plant. These broader applications range from other pome fruits, such as pears and to stone fruits, such as peaches and cherries.

In compliance with the statutes, the invention has been described in language more or less specific as to structural features and process steps. While this invention is susceptible to embodiment in different forms, the specification illustrates preferred embodiments of the invention with the understanding that the present disclosure is to be considered an exemplification of the principles of the invention, and the disclosure is not intended to limit the invention to the particular embodiments described. Those with ordinary skill in the art will appreciate that other embodiments and variations of the invention are possible, which employ the same inventive concepts as described above. Therefore, the invention is not to be limited except by the following claims, as appropriately interpreted in accordance with the doctrine of equivalents.

What is claimed is:

1. A process for thinning fruit blossoms, which comprises applying an effective amount of a blossom thinning composition to the blossoms of a fruit bearing plant, the blossom thinning composition consisting essentially of calcium chloride ($CaCl_2$) as an active ingredient for the purpose of blossom thinning.

2. The process of claim 1, wherein the calcium chloride is applied in a substantially aqueous solution.

3. The process of claim 1, wherein the fruit bearing plants are fruit trees.

4. The process of claim 3, wherein the fruit trees are apple trees.

5. The process of claim 1, wherein the calcium chloride is applied in a substantially aqueous solution consisting essentially of calcium chloride at a concentration of between 5 pounds and 40 pounds of the calcium chloride per an acre of the fruit bearing plants.

6. The process of claim 1, wherein the calcium chloride is applied in a substantially aqueous solution consisting essentially of calcium chloride brine diluted to a concentration of approximately 1 pound of the calcium chloride per 10 gallons of water.

7. The process of claim 1, wherein the calcium chloride is applied in a substantially aqueous solution consisting essentially of calcium chloride brine diluted to a concentration of approximately between approximately ¼ pound of the calcium chloride to 2 pounds of the calcium chloride per 10 gallons of water.

8. The process of claim 1, wherein the calcium chloride is applied at a rate of approximately 20 pounds of the calcium chloride per acre of the fruit bearing plant.

9. The process of claim 1, wherein the fruit bearing plants are fruit trees.

10. A composition for thinning fruit blossoms, applying an effective amount of a blossom thinning composition to the blossoms of a fruit bearing plant, the blossom thinning composition consisting essentially of a calcium chloride ($CaCl_2$) as an active ingredient for the purpose of blossom thinning.

11. The composition of claim 10, wherein the calcium chloride is applied in a substantially aqueous solution.

12. The composition of claim 10, wherein the calcium chloride is applied in a substantially aqueous solution consisting essentially of calcium chloride at a concentration of between 5 and 40 pounds of the calcium chloride per an acre of the fruit bearing plants.

13. The composition of claim 10, wherein the calcium chloride is applied in a substantially aqueous solution consisting essentially of calcium chloride brine diluted to a concentration of approximately 1 pound of the calcium chloride per 10 gallons of water.

14. The composition of claim 10, wherein the calcium chloride is applied at a rate of approximately 20 pounds of the calcium chloride per acre of the fruit bearing plant.

15. The composition of claim 10, wherein the calcium chloride is applied in a substantially aqueous solution consisting essentially of calcium chloride brine diluted to a concentration between approximately ¼ pound of the calcium chloride to 2 pounds of the calcium chloride per 10 gallons of water.

* * * * *